(12) United States Patent
Haskell

(10) Patent No.: US 7,175,860 B2
(45) Date of Patent: Feb. 13, 2007

(54) ENHANCED WOUND HEALING METHOD AND COMPOSITION

(75) Inventor: Weston Haskell, Fulshear, TX (US)

(73) Assignee: Haskell Pharmaceuticals, Inc., Brookshire, TX (US)

( * ) Notice: Subject to any disclaimer, the term of this patent is extended or adjusted under 35 U.S.C. 154(b) by 422 days.

(21) Appl. No.: 10/909,481

(22) Filed: Aug. 2, 2004

(65) Prior Publication Data

US 2006/0024395 A1 Feb. 2, 2006

(51) Int. Cl.
*A61K 36/00* (2006.01)

(52) U.S. Cl. ...................... 424/769; 424/776

(58) Field of Classification Search ...................... None
See application file for complete search history.

(56) References Cited

U.S. PATENT DOCUMENTS

| | | | |
|---|---|---|---|
| 2,351,434 A * | 6/1944 | Jessen et al. ................ | 507/104 |
| 3,376,191 A * | 4/1968 | Reeves ........................ | 514/132 |
| 4,035,483 A | 7/1977 | Bunyan | |
| 4,098,765 A * | 7/1978 | Kays et al. .................... | 528/1 |
| 4,857,326 A | 8/1989 | Stitt | |
| 5,843,987 A | 12/1998 | Rajagopalan et al. | |
| 5,855,922 A | 1/1999 | Danner | |
| 6,033,573 A | 3/2000 | Toles et al. | |
| 6,060,101 A | 5/2000 | Erasmus et al. | |
| 6,165,539 A | 12/2000 | Erasmus et al. | |
| 6,271,214 B1 | 8/2001 | Qiu | |
| 6,664,287 B2 * | 12/2003 | Avery et al. ................. | 514/436 |
| 2001/0022980 A1 | 9/2001 | Bell et al. | |
| 2003/0104075 A1 | 6/2003 | Chevaux et al. | |
| 2004/0067224 A1 | 4/2004 | Ernest | |
| 2004/0161482 A1 * | 8/2004 | Kawada et al. ............. | 424/771 |

FOREIGN PATENT DOCUMENTS

JP 2000-072686 * 3/2000

OTHER PUBLICATIONS http://www.fungusfocus.com/html/black_walnut.htm; pp. 1-3.
http://www.uga.edu/fruit/walnut.htm; pp. 1-11.
http://www.wvu.edu/~agexten/hortcult/fruits/blkwalnt.htm; pp. 1-3.
Potts, Pathogenic bacteria attach to human fibronectin through a tandem beta-zipper, Nature, vol. 423, pp. 177-181 (May 3, 2003) (Abstract).
Berendt, Bacterial fibronectin-binding proteins and endothelial cell surface fibronectin mediate adherence of . . . , Microbiology, vol. 145, pp. 3477-3486 (1999).
http://www.fungusfocus.com/html/black_walnut.htm.
http://www.uga.edu/fruit/walnuts.pdf.
http://www.wvu.edu/~agexten/hortcult/fruits/blkwalnt.htm.
Potts, Nature 423, 177-181 (2003).
Berendt, Microbiology 145, 3477-3486 (1999).

* cited by examiner

*Primary Examiner*—Christopher R. Tate
(74) *Attorney, Agent, or Firm*—Keith R. Derrington

(57) ABSTRACT

A composition extracted from nut husks including a method of forming the composition, where the composition is useful in healing wounds. The method includes collecting pecan husks, pressing the pecan husks thereby expressing fluid from the husks, and collecting the expressed fluid. The extraction process is conducted in an inert environment thereby preventing oxidation of the expressed fluid. After collection, the expressed fluid can be transferred to storage prior to use, such as in foil packets or glass tubes.

16 Claims, 3 Drawing Sheets

ENHANCED WOUND HEALING METHOD AND COMPOSITION

BACKGROUND OF THE INVENTION

1. Field of the Invention

The invention relates generally to a natural antiseptic and prophylactic agent. The invention also relates to a composition useful for healing wounds. The invention further relates to a process of collecting, storing, and applying the composition, where the process maintains the composition within an inert environment thereby preventing degradation of the composition.

2. Description of Related Art

Many methods and compositions exist for promoting the speed of wound healing. These include ensuring the wound is cleaned as soon as possible to remove bacterial or septic agents that might cause the wound to become infected. Other methods involve isolating the wounded area within an oxygen rich environment to enhance the healing process. Compositions for aiding in wound healing include a myriad of antiseptic compounds, antibacterial agents, and others such as polysaccharides. Examples of these and other methods and compositions can be found in the following references: U.S. Pat. No. 6,271,214, U.S. Pat. No. 4,035,483, and U.S. Pat. No. 5,855,922.

However the methods taught in each of the aforementioned references suffers from the drawback that the operative composition attacks or reacts with pathogens in the region where the composition is applied. Thus once the anti-pathogen effect of the composition expires, the wound can become invaded and thus infected from later arriving pathogens. It is known that pathogenic bacteria attach and invade skin cells via a specific local mechanism, as discussed by Potts (Jennifer R. Potts, et al., Nature 423, 177–181 (2003). "Pathogenic bacteria attach to human fibronectin through a tandem beta-zipper") and Berendt (Berendt, A. R., et al., Microbiology 145, 3477–3486 (1999) "Bacterial fibronectin-binding proteins and endothelial cell surface fibronectin mediate adherence of *Staphylococcus aureus* to resting human endothelial cells.") Thus if the would is left unprotected at a time when pathogens come into contact with the wound, the wound can become possibly infected.

Therefore, a need exists for a composition, and a method of making the composition, where the composition can be applied to a wound and protect the wound from pathogen infection.

BRIEF SUMMARY OF THE INVENTION

The present invention includes a method of producing a wound healing agent comprising, collecting pecan husks, disposing the pecan husks in an inert environment, pressing the pecan husks within the inert environment at a pressure adequate for expressing liquid from the pecan husks, and collecting the expressed liquid from the pecan husks. The method can further comprise storing the expressed liquid in a container having a sealed inert environment within. The pressure applied to the pecan husks can be at least 3000 to 10,000 pounds per square inch, alternatively the pressure can be about 5,000 pounds per square inch. The method of the present invention can further comprise applying the expressed liquid itself to a wound, or applying the stored expressed liquid to a wound. The container can be a glass bottle or a packet. Furthermore, the present invention can comprise applying the expressed liquid onto an application gauze and storing the application gauze having the applied expressed liquid within the packet.

The present invention involves a wound healing kit comprising a sealable container having an inert environment within and an elixir comprising liquid expressed from pecan husks while in an inert environment, where the elixir is disposed within the container. The container can be comprised of a glass tube or a packet. The wound healing kit can further comprise a gauze pad disposed within the packet and wetted with the expressed liquid. The elixir of the present invention can be formed by applying a pressure onto the pecan husks of from 5000 pounds per square inch to about 10,000 pounds per square inch. Alternatively, the applied pressure can be about 5000 pounds per square inch.

DETAILED DESCRIPTION OF THE INVENTION

While it had been known that the husks of certain nuts, such as from black walnuts, contained compounds that possessed antiseptic like qualities, it was not known that the presence of oxygen could oxidize these compounds and eliminate their prophylactic qualities. It was also believed that the compounds having these qualities included juglone and possibly tannic acid. However it has been discovered that tannic acid is possibly a product produced by oxidation of compounds naturally occurring within nut husks, more notably pecan husks, where these naturally occurring compounds are actually precursors via oxidation to tannic acid. These precursors to tannic acid exist in addition to juglone. Thus subjecting the pecan husk extract to the oxygen in ambient air results in oxidation, that in turn alters the characteristics of the extract and negates some of the antiseptic qualities and negates completely the prophylactic qualities of the extract. However if the naturally occurring fluid within a pecan husk, or the husk of nut similar to a pecan such as a black walnut, were extracted in an inert environment substantially void of the presence of oxygen; this elixir from the pecan husk or any similar fluids, could be preserved for use long after the fluid was extracted from the husk.

Figure 1:
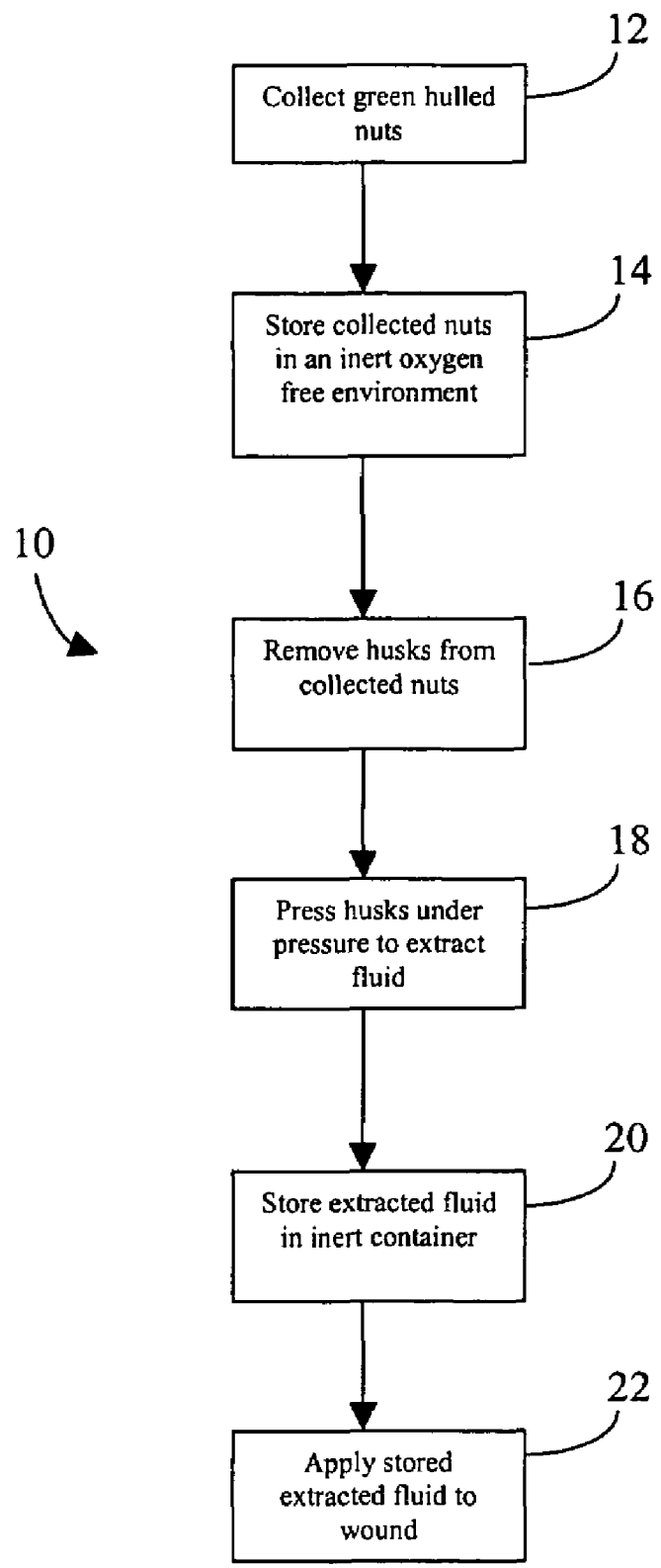
FIG. 1 illustrates a step-by-step method of the present invention.

With reference to the drawing herein, one embodiment of a method of producing and using a wound healing elixir is shown in FIG. 1. The embodiment of the production method 10 of FIG. 1 includes a step 12 of harvesting a quantity of green hull pecans for processing. The pecans should be collected from their tree before they have fallen. After the pecans have fallen to the ground the yield of liquids from the green husk is greatly reduced or eliminated. Optionally nuts from other trees can be substituted in this process, such as black walnut, butternut, and English walnut.

As seen in step 14, after the nuts have been collected they should be placed into a container (not shown) having inert space that has been purged of all oxygen. Examples of an inert space include a glove bag inflated with pure argon gas to displace all air from the bag. The ambient air that would typically be within the inert space is replaced with an inert gas such as nitrogen, argon, carbon dioxide, and helium among others. Preferably the gas used is heavier than air (i.e. argon or carbon dioxide) thus slowly adding the gas to the bottom of the container can displace the air within the container. When substantially all of the oxygen has been removed or displaced from the inert space the husks can then be removed from the nuts (step 16). Removing the husks can be done manually or by using a "shuck brush" as is currently used by commercial orchards.

After being removed from the rest of the raw nut, the husks are transported to a press and squeezed at a pressure sufficient to extract the fluid naturally present within the pecan husk (step 18). Preferably the pressure applied while pressing the fluid from the husks is around 5000 pounds per square inch. Following the pressing function of step 18 the naturally occurring fluid within the green husk is stored for later use or in an interim storage prior to the final packaging of the extracted fluid. Whether the fluid is stored in an interim container or in its final package, both the container and the package must be substantially free of oxygen. As previously noted, the fluid extracted from the husks is susceptible to oxidation, and the presence of oxygen has a deleterious effect on the wound healing properties of the fluid. Final packaging of the extracted fluid can involve storing the extracted fluid within bottles, sealed packets, or capsules.

With respect to storing the extracted fluid 30 within a bottle 24, it is preferred that the bottle be sealed with a foil or foil like membrane (not shown) adhered to the opening of the bottle 24. Additionally, a removable cap 26 can be provided along with the bottle 24 thereby providing a barrier seal on the bottle 24 that can further prevent exposure of the extracted fluid 30 to ambient air and other sources of oxygen. While the bottle 24 can be any size, one optional size is one that would accommodate approximately 2–4 mls of extracted liquid 30. Optionally, 30 ml glass bottles with screw top with a tin-foil lined cap can be used, up to larger bottles having a capacity in excess of four liters.

Figure 3:
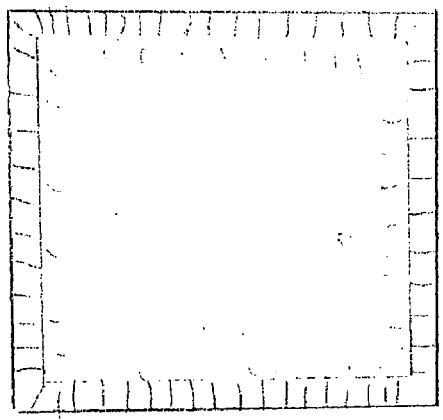
FIG. 3 portrays in side view a packet container.
Figure 2:
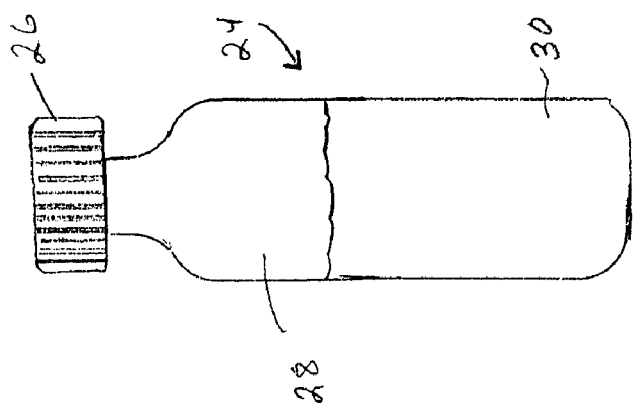
FIG. 2 depicts a side view of extracted liquid stored within a bottle.

With reference now to FIG. 3, an embodiment of a packet 32 of the present invention is illustrated. As shown the packet 32 is comprised of a pair of largely rectangular sides joined at their outer periphery, optionally the sides could be other shapes, such as circular or elliptical. An amount of the extracted fluid is stored within the packet 32 in an airtight environment. The packet 32 should be openable either by hand, but can also be opened with scissors or some other cutting instrument. The material of the packet 32 can be foil, plastic, a thermoplastic material, a polymeric material, or any other material that provides an atmospheric barrier, is sealable, and can be opened without undue effort. Optionally gauze 34 can be included within the packet 32, where the gauze 34 is wetted with the extracted liquid 30 prior to being stored within the packet 32. Preferably the gauze 34 is comprised of a sterile cotton or cotton like material, but can be made of any material capable of withholding a sufficient amount of extracted liquid 30 within its fibers for later application to a wound. Selection and use of an appropriate bottle 24, cap 26, packet 32, and gauze 34 is well within the capabilities of one of ordinary skill in the art.

Figure 4:
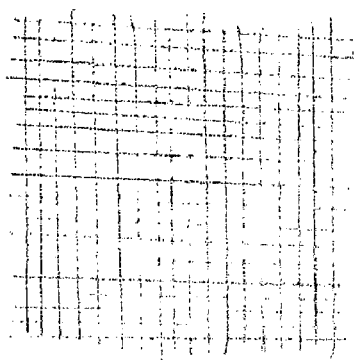
FIG. 4 shows an overhead view of a gauze patch.
Figure 5:
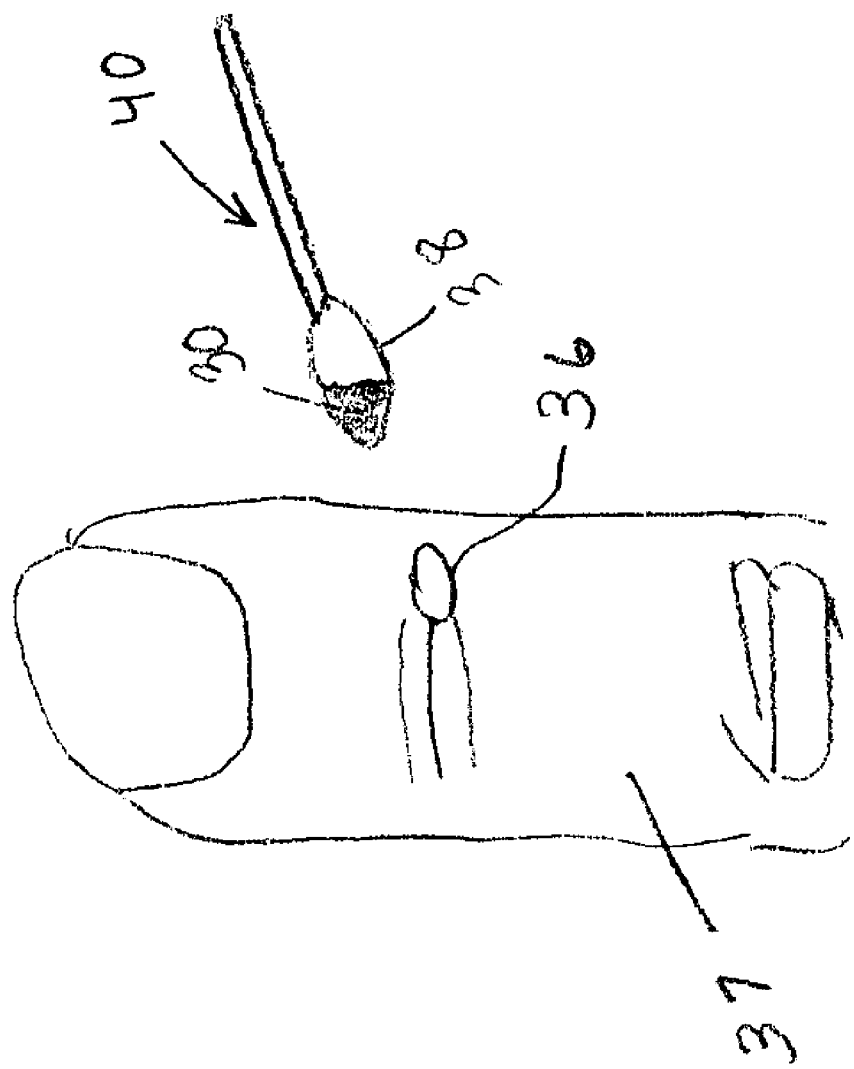
FIG. 5 illustrates application of the liquid extract onto a wound.

In use, the extracted liquid 30 is applied to a wound 36 and to the skin area surrounding the wound 36. While the wound 36 of FIG. 5 is shown on a human digit 37, a wound 36 located on any part of a body can be treated with the liquid of the present invention. As shown, the extracted liquid 30 has been applied to the tip 38 of a cotton swab 40 for application onto the wound 36. However the wound 36 could be treated with the wetted gauze 34 of FIG. 4, where the gauze 34 had been wetted with the extracted fluid 30 from the bottle 24, stored within the packet 32, or wetted with the extracted fluid 30 straight from the press.

EXAMPLE

In one non-limiting example of use of the present invention, a 76 year old human subject sustained an injury involving damaged skin on his right shin about three inches above the ankle. The injury included superficial skin damage and slight bleeding. The extracted liquid of the present invention was immediately applied after the injury. A second application of the liquid was applied approximately an hour after the first application. Until the next day, the subject avoided wetting the injury. Sixteen days later the injury was completely healed within any additional intervention. Additionally, at no time did the wound become infected or exhibit an infectious appearance. It is believed that adsorption of the extracted liquid onto the skin protected against infection during the subject's healing process. The subject applied the extracted liquid on four separate occasions, to four separate wounds with the same result; namely none of the wounded areas became infected and hence all healed without complications and in a timely fashion.

Testing indicates that the expressed liquid is toxic to certain cells. The implication of this is that a long lasting protective action of the extracted liquid arises from a barrier created by adsorption of the extracted liquid on the critical cell surface membrane. Thus it has been concluded that application of the expressed liquid onto a wound provides a prophylactic effect onto the wound and protects the wound against pathogens being introduced into the wound. Protecting a wound against such pathogens can in turn prevent any infection of the wound and speed the healing of the wound.

The present invention described herein, therefore, is well adapted to carry out the objects and attain the ends and advantages mentioned, as well as others inherent therein. While a presently preferred embodiment of the invention has been given for purposes of disclosure, numerous changes exist in the details of procedures for accomplishing the desired results. These and other similar modifications will readily suggest themselves to those skilled in the art, and are intended to be encompassed within the spirit of the present invention disclosed herein and the scope of the appended claims.

What is claimed is:

1. A method of producing a wound healing agent comprising:
   collecting pecan husks;
   disposing the pecan husks in an inert environment;
   pressing the pecan husks, within the inert environment, at a pressure adequate for expressing liquid from the pecan husks; and
   collecting the expressed liquid from the pecan husks.

2. The method of claim 1 further comprising storing the expressed liquid in a container having a sealed inert environment within.

3. The method of claim 1 wherein the pressure applied to the pecan husks at least 3000 to 10,000 pounds per square inch.

4. The method of claim 1 wherein the pressure applied to the pecan husks is about 5000 pounds per square inch.

5. The method of claim 1 further comprising applying the expressed liquid to a wound.

6. The method of claim 2 further comprising applying the stored expressed liquid to a wound.

7. The method of claim 2, wherein said container comprises a glass bottle.

8. The method of claim 2, wherein said container comprises a packet.

9. The method of claim 8 further comprising applying said expressed liquid onto an application gauze and storing the application gauze having the applied expressed liquid within said packet.

10. The method of claim 1, wherein application of said expressed liquid onto a wound provides a prophylactic effect onto the wound thereby preventing the introduction of pathogens into the wound.

11. A wound healing kit comprising:
   a sealable container having an inert environment within; and
   an elixir comprising liquid expressed from pecan husks while in an inert environment,
   said elixir disposed within said container.

12. The wound healing kit of claim 11 wherein said container is comprised of a glass tube.

13. The wound healing kit of claim 11 wherein said container is comprised of a packet.

14. The wound healing kit of claim 13 further comprising a gauze pad disposed within said packet and wetted with said expressed liquid.

15. The would healing kit of claim 11 wherein said elixir is produced by applying a pressure onto the pecan husks of from 5000 pounds per square inch to about 10,000 pounds per square inch.

16. The wound healing kit of claim 11 wherein said elixir is produced by applying a pressure onto the pecan husks of about 5000 pounds per square inch.

* * * * *